United States Patent
Oraevsky et al.

(10) Patent No.: US 6,309,352 B1
(45) Date of Patent: Oct. 30, 2001

(54) REAL TIME OPTOACOUSTIC MONITORING OF CHANGES IN TISSUE PROPERTIES

(75) Inventors: Alexander A. Oraevsky, Houston; Rinat O. Esenaliev, Galveston; Massoud Motamedi, League City; Alexander A. Karabutov, Galveston, all of TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 09/179,791

(22) Filed: Oct. 27, 1998

Related U.S. Application Data

(63) Continuation-in-part of application No. 08/594,758, filed on Jan. 31, 1996, now Pat. No. 5,840,023.

(51) Int. Cl.[7] .............................. A61B 6/00; G03B 42/06
(52) U.S. Cl. ......................... 600/407; 600/439; 600/586; 607/100; 367/7
(58) Field of Search ................................. 600/407, 473, 600/476, 310, 586, 439, 461, 463, 431; 606/3, 10–13, 14–16, 38; 73/587, 606; 367/7; 604/22; 128/916; 607/101, 88, 100; 378/65

(56) References Cited

U.S. PATENT DOCUMENTS

| | | |
|---|---|---|
| 4,028,933 | 6/1977 | Lemons et al. . |
| 4,212,206 | 7/1980 | Hartemann et al. . |
| 4,255,971 * | 3/1981 | Rosencwaig ............................. 73/606 |
| 4,267,732 * | 5/1981 | Quate ..................................... 73/606 |
| 4,385,634 | 5/1983 | Bowen et al. . |
| 4,430,897 | 2/1984 | Quate . |
| 4,594,662 * | 6/1986 | Devaney ................................ 364/400 |
| 4,710,030 | 12/1987 | Tauc et al. . |
| 4,727,420 | 2/1988 | Kohda et al. . |
| 5,041,121 | 8/1991 | Wondrazek et al. . |
| 5,136,172 | 8/1992 | Nakata et al. . |
| 5,141,331 | 8/1992 | Oehler et al. . |
| 5,158,560 * | 10/1992 | Sogawa et al. ......................... 606/15 |
| 5,161,125 * | 11/1992 | Maccabee .............................. 367/99 |
| 5,178,836 | 1/1993 | Kitamori et al. . |
| 5,207,672 * | 5/1993 | Roth et al. ............................. 606/10 |
| 5,254,112 | 10/1993 | Sinofsky et al. . |
| 5,293,873 | 3/1994 | Fang . |
| 5,398,685 | 3/1995 | Wilk et al. . |
| 5,417,653 * | 5/1995 | Sahota et al. . |
| 5,421,337 | 6/1995 | Richards-Kortum et al. . |
| 5,444,541 * | 8/1995 | Small et al. ........................ 356/432 |
| 5,465,722 | 11/1995 | Fort et al. . |
| 5,554,810 * | 9/1996 | Anifrani et al. ....................... 73/801 |
| 5,582,578 | 12/1996 | Zhong et al. . |
| 5,583,634 | 12/1996 | Andre et al. . |

(List continued on next page.)

FOREIGN PATENT DOCUMENTS

WO 97/27801    8/1997   (WO) .

OTHER PUBLICATIONS

Esenaliev et al., "Axial Resolution of Laser Optoacoustic Imaging: Influence of Acoustic Attenuation and Diffraction," *SPIE*, 3254:294–306 (1998).

(List continued on next page.)

*Primary Examiner*—Marvin M. Lateef
*Assistant Examiner*—Shawna J Shaw
(74) *Attorney, Agent, or Firm*—Baman & Rogalskyj, LLP

(57) ABSTRACT

The present invention is directed to a method/system of for monitoring tissue properties in real time during treatment using optoacoustic imaging system. Optoacoustic monitoring provides a control of the extent of abnormal tissue damage and assures minimal damage to surrounding normal tissues. Such technique can be applied for monitoring and controlling during surgical, therapeutic, and cosmetic procedures performed in various tissues and organs.

38 Claims, 13 Drawing Sheets

U.S. PATENT DOCUMENTS

| | | | |
|---|---|---|---|
| 5,588,428 | * | 12/1996 | Smith et al. ............... 128/653.1 |
| 5,602,894 | | 2/1997 | Bardash . |
| 5,615,675 | * | 4/1997 | O'Donnell et al. ............ 128/653.1 |
| 5,662,590 | * | 9/1997 | De La Torre et al. ................ 601/2 |
| 5,713,356 | * | 2/1998 | Kruger ............................ 128/653.1 |
| 5,718,231 | * | 2/1998 | Dewhurst et al. ............ 128/662.06 |
| 5,722,406 | * | 3/1998 | Papaioannou ................ 128/653.1 |
| 5,840,023 | * | 11/1998 | Oraevsky et al. ................ 600/407 |
| 5,897,494 | * | 4/1999 | Flock et al. ...................... 600/407 |
| 5,902,237 | * | 5/1999 | Glass ................................ 600/407 |
| 5,924,986 | * | 7/1999 | Chandler et al. ................ 600/407 |
| 5,944,687 | * | 8/1999 | Benett et al. ...................... 604/22 |
| 5,977,538 | * | 11/1999 | Unger et al. .................... 250/227.2 |

OTHER PUBLICATIONS

Oraevsky, et al., "Laser Optacoustic Tomography of Layered Tissues: Signal Processing", *SPIE*, 2979:59–70 (1997).

Esenaliev et al., "Laser Optoacoustic Imaging for Breast Cancer Diagnostics: Limit of Detection and Comparison with X–ray and Ultrasound Imaging," *SPIE*, 2979:71–82 (1997).

Oraevsky et al., "Measurement of Tissue Optical Properties by Time–Resolved Detection of Laser–Induced Transient Stress," *Applied Optics*, 36(1):402–415 (1997).

Agah et al., "Dynamics of Temperature Dependent Optical Properties of Tissue: Dependence on Thermally Induced Alteration," *IEEE Transactions on Biomedical Engineering*, 43(8):839–846 (1996).

Esenaliev et al., "Laser Opto–acoustic Tomography for Medical Diagnostics: Experiments with Biological Tissues," *SPIE*, 2676:84–90 (1996).

Karabutov et al., "Time–resolved Laser Optoacoustic Tomography of Inhomogeneous Media," *Appl. Phys. B*, 63:545–563 (1996).

Kim et al., "Nonlinear Finite–Element Analysis of the Role of Dynamic Changes in Blood Perfusion and Optical Properties in Laser Coagulation of Tissue," *IEEE Journal of Selected Topics in Quantum Electronics*, 2(4):922–933 (1996).

Oraevsky et al., "Laser Opto–Acoustic Imaging of Turbid Media: Determination of Optical Properties by Comparison With Diffusion Theory and Monte Carlo Simulation," *SPIE*, 2681:277–284 (1996).

Oraevsky et al., "Laser Opto–Acoustic Tomography for Medical Diagnostics: Principles," *SPIE*, 2676:22–31 (1996).

Oraevsky et al., "Breast Cancer Diagnostics by Laser Opto–Acoustic Tomography," in Alfano et al., ed., *Trends in Optics and Photonics. TOPS vol. II. Advances in Optical Imaging and Photon Migration*, pp. 316–321 (1996).

Oraevsky, "Laser Optoacoustic Imaging for Diagnostics of Cancer," *LEOS Newsletter*, pp. 17–20 (Dec. 1996).

Motamedi et al. "Laser Photocoagulation of Prostate: Influence of Dosimetry," *Lasers in Surgery and Medicine*, 17:49–58 (1995).

Oravesky et al., "Lateral and Z–Axial Resolution in Laser Optoacoustic Imaging With Ultrasonic Transducers," *SPIE*, 2389:198–208 (1995).

Vijverberg et al., Evaluation of a Time–resolved Stress Detection Method to Determine Tissue Optical Properties, *Proc. SPIE*, 2323:312–316 (1995).

Oraevsky et al., "Time–Resolved Optoacoustic Imaging in Layered Biological Tissues," in Alfano, ed., *OSA Proceedings on Advances in Optical and Photon Migration*, 21:161–165 (1994).

Oravesky et al., "Laser–Based Optoacoustic Imaging in Biological Tissues," *SPIE*, 2134:122–128 (1994).

Thomsen et al., "Optical Properties of Albino Rat Skin Heated In Vitro: Comparison of Photoacoustic and Integrating Sphere Measurement Techniques," *SPIE*, 2134A:106–113 (1994).

* cited by examiner

REAL TIME OPTOACOUSTIC MONITORING OF CHANGES IN TISSUE PROPERTIES

Cross-reference to Related Application

This patent application is a continuation-in-part of U.S. application Ser. No. 08/594,758, filed Jan. 31, 1996 now U.S. Pat. No. 5,840,023 issued Nov. 24, 1998.

BACKGROUND OF THE INVENTION

1. Field of the Invention

The present invention relates generally to the fields of imaging, thermotherapy, and cryotherapy. More specifically, the present invention relates to a method and system utilizing optoacoustic imaging to monitor, in real time, tissue properties during therapeutic or surgical treatment.

2. Description of the Related Art

Various types of therapeutic agents (radiation, heating, cooling, drugs, surgical tools) are being used for treatment. It is necessary to monitor tissue physical properties during treatment to provide selective damage to diseased tissues. This will result in better outcome of any treatment procedure. It is highly desirable to develop an imaging technique which will be capable of monitoring tissue physical parameters in real time during treatment. Such an imaging technique will provide feed-back information which will be used to optimize treatment procedure. All conventional imaging techniques have limitations such as low contrast (ultrasound and X-ray imaging), high cost (MRI, PET), poor resolution (PET). Some of them are not capable of providing imaging information in real time. Due to these limitations, these conventional techniques are not being widely applied for monitoring tissue physical properties in real time during treatment.

It has been demonstrated that thermally treated tissues possess optical properties that are significantly different from normal untreated tissues. For example, the optical properties of coagulated and normal tissues are different. It was also demonstrated that different regimes of coagulation may yield different end values of tissue optical properties. A hemorrhage ring was observed at the boundary between coagulated and normal tissue in vivo.

The prior art is deficient in the lack of effective means of monitoring of tissue parameters in real time during therapeutic or surgical treatment. The present invention fulfills this long-standing need and desire in the art.

SUMMARY OF THE INVENTION

The present invention is directed to a method/system of real-time optoacoustic monitoring of tissue physical properties with the purpose of providing selective damage of diseased tissues and assuring minimal damage to surrounding normal tissues during therapy.

In one embodiment of the present invention, there is provided a method of monitoring tissue properties in real time during treatment using a laser optoacoustic imaging system, comprising the steps of administering a treatment agent to the tissue and applying the optoacoustic imaging system to the treated tissue. Preferably, the tissue can be selected from various organs with tumors or other lesions, and the tissue properties are referred to physical dimension, optical absorption, optical scattering, optical attenuation coefficient, temperature, thermal expansion coefficient, speed of sound or heat capacity. Representative treatment agents include optical radiation, electromagnetic radiation, ultrasonic radiation, electrical current, heating, cooling, a drug or a surgical tool.

In another embodiment of the present invention, there is provided a system of monitoring tissue properties in real time during treatment, comprising a system for administering a treatment agent to the tissue; an optoacoustic imaging system for providing images; an exogenous molecular probe for reflecting the treatment; and a feed-back electronic system for adjusting parameters of the treatment agent.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1:
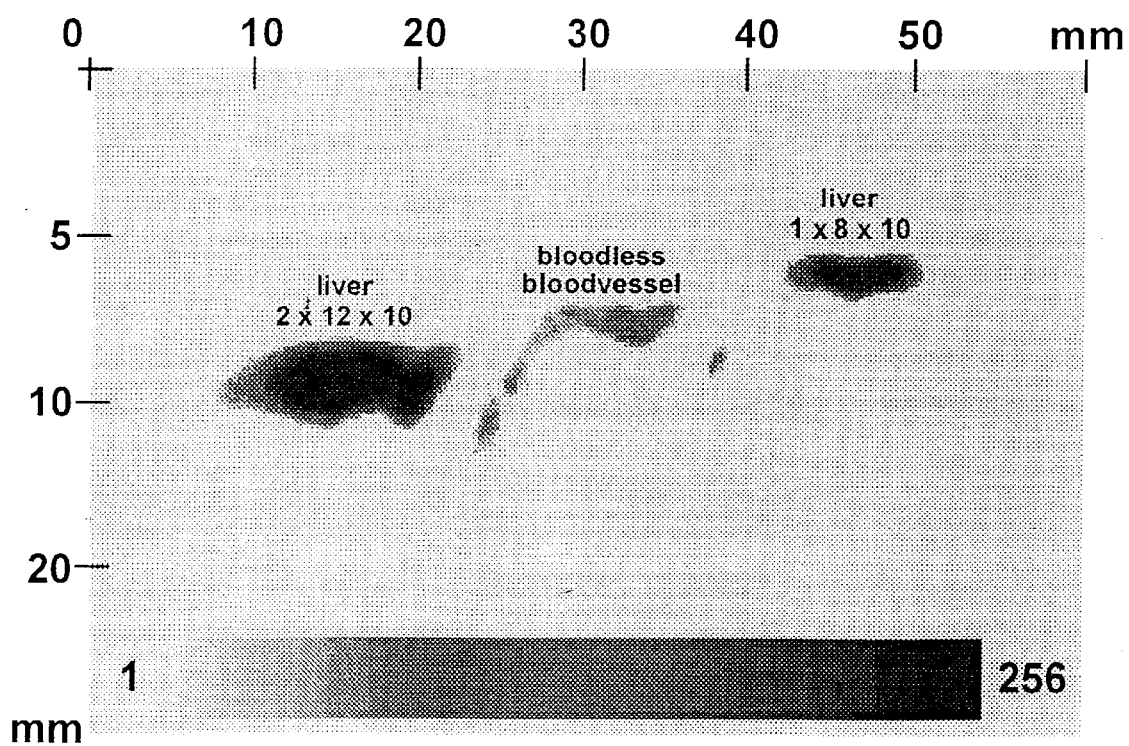
FIG. 1 shows an optoacoustic image obtained in vitro from two pieces of liver tissue simulating tumors with increased absorption embedded in a tissue with lower absorption (1 pixel=0.1 mm).

Laser optoacoustic imaging is an imaging technique recently proposed for medical diagnostics (screening). Laser optoacoustic imaging has potential to become an imaging technique with high contrast, sensitivity and resolution, and of moderate cost.

In the present invention, application of laser optoacoustic imaging is proposed for tissue physical properties monitoring during treatment in real time. Application of radiation, heating, or cooling induces changes in tissue temperature and optical and thermophysical properties. Optoacoustic technique is sensitive to changes in tissue temperature, optical properties (absorption, scattering and effective attenuation coefficient), and the following thermophysical parameters: Gruneisen coefficient, thermal expansion coefficient, speed of sound, and heat capacity at constant pressure.

In the present invention, laser interstitial coagulation is used for treatment of malignant tumors, which is based on heating of tumors by laser radiation resulting in coagulation and death of cancer cells. There is a need to monitor the degree of coagulation and the dimensions of the coagulation zone to avoid unwanted thermal damage to normal tissues surrounding the tumor.

The present invention demonstrates that optoacoustic signals measured in normal and coagulated tissues are different. In particular, the absorption and scattering coefficient of coagulated tissue is higher than that of normal tissue. Experiments were conducted demonstrating that the changes in the optical properties can be detected during laser coagulation in real time. This technique can be applied if any other type of radiation (microwave, radiofrequency, ultrasonic, etc.) is used for tissue heating. The invention can potentially be used for precise monitoring of interstitial coagulation of tumors in various organs such as breast, prostate, etc. It is proposed that laser optoacoustic can also be used for monitoring of interstitial coagulation during treatment of benign lesions. One of the most important applications is monitoring prostate tissue coagulation during treatment of benign prostatic hyperplasia.

Also disclosed in the present invention is laser optoacoustic monitoring of tissue temperature during hyperthermia. Hyperthermia has a great potential for treatment of malignant lesions in many organs. Temperature monitoring during these procedures is vital for successful treatment. Laser optoacoustic imaging is capable of non-invasive detection of 1° C. temperature change at the depth of up to several centimeters in some tissues. All the conventional imaging techniques fail to detect a temperature change at this depth in tissue.

Further disclosed in the present invention are applications of laser optoacoustic monitoring for other types of therapy. For example, cryotherapy is being widely used for treatment. There is a need to monitor dimensions of frozen zone during the cryotherapy to avoid unwanted damage to normal tissues. Optical and thermophysical properties of normal and frozen tissues are different providing high contrast in optoacoustic images. The movement of boundary between normal and frozen tissues should be clearly seen. Therefore, the optoacoustic monitoring can be used for monitoring physical properties of tissue during cryotherapy in real time.

Administration of drugs can change optical properties of tissue. For instance, application of photosensitizers for photodynamic therapy increases optical absorption coefficient of tissue. This can be used to study pharmacokinetics of the photosensitizers before, during, and after treatment.

Surgical tools have optical and acoustic properties substantially different from tissue properties. Along with optical contrast between normal and tumor tissue, it is possible to use this technique for navigation during surgery or biopsy.

In one embodiment of the present invention, there is provided a method of monitoring tissue properties in real time during treatment using an laser optoacoustic imaging system, comprising the steps of administering a treatment agent to the tissue and applying the optoacoustic imaging system to the treated tissue.

In a preferred embodiment, the tissue can be selected from various organs with tumors or other lesions. Representative organs which can be examined using this technique include liver, kidney, breast, prostate, brain, heart, eye and blood vessels. Alternatively, the tissue is from mucosa of a hollow organ, such as oral cavity, gastrointestinal tract, intestine, colon, rectum, bladder and vagina.

In another preferred embodiment, the tissue properties are referred to physical dimension, optical absorption, optical scattering, optical attenuation coefficient, temperature, thermal expansion coefficient, speed of sound or heat capacity. Specifically, the optical radiation is generated from a laser or non-laser source and is in the spectral range from about 0.2 $\mu$m to about 200 $\mu$m. More specifically, the optical radiation and optical pulses for imaging are delivered through the same fiber-optic delivery system. Still specifically, the electromagnetic radiation is in radiofrequency, or in microwave spectral range, or simply a X-ray radiation, or a gamma radiation.

In still another preferred embodiment, the treatment agent can be an optical radiation, an electromagnetic radiation, an ultrasonic radiation, an electrical current, heating, cooling, a drug or a surgical tool.

In another embodiment of the present invention, there is provided a system of monitoring tissue properties in real time during treatment, comprising a system for administering a treatment agent to the tissue; an optoacoustic imaging system for providing images; an exogenous molecular probe for reflecting the treatment; and a feed-back electronic system for adjusting parameters of the treatment agent.

The following examples are given for the purpose of illustrating various embodiments of the invention and are not meant to limit the present invention in any fashion.

EXAMPLE 1

Monitoring of Interstitial Coagulation of Tumors

Liver samples simulating tumors were placed between two pieces of chicken breast muscle tissue. Pulsed Nd:YAG laser radiation is used to obtain the image (see FIG. 1). A blood vessel in the chicken breast tissue is also visible. The data demonstrates capability of an optoacoustic technique to reconstruct images in tissue on the basis of the contract in optical and thermophysical properties between these two tissues. This allows monitoring of the tissue properties during treatment because application of a treatment agent (heating, freezing, etc.) will induce changes in optoacoustic images.

Figure 2:
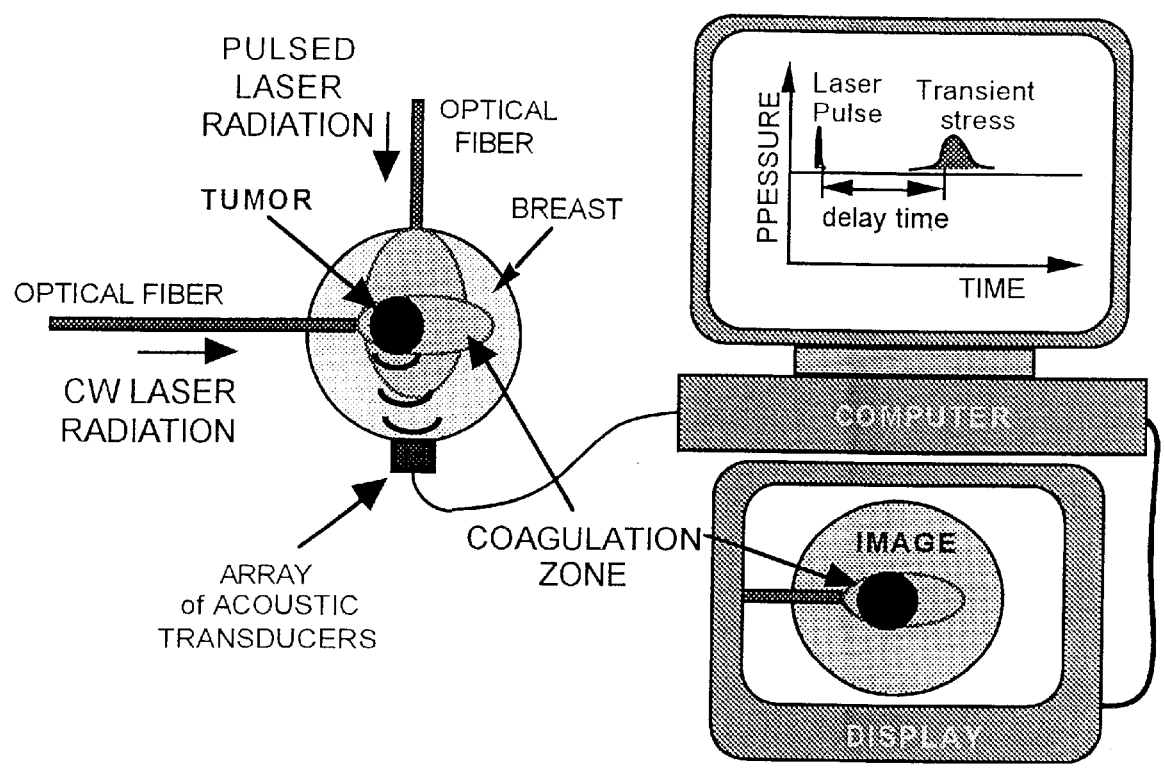
FIG. 2 shows an example of utility for laser optoacoustic imaging system for monitoring of laser coagulation of a tumor within large volume of normal tissue.

FIG. 2 demonstrates an example of utility for laser optoacoustic imaging in monitoring of tissue optical properties during coagulation of a breast tumor by a continuous wave laser radiation. An optical fiber is used to deliver interstitially the laser radiation to the tumor. The fiber can be introduced into the breast tissue using a needle. The needle can be removed from the breast before the continuous wave laser irradiation. The continuous wave irradiation results in coagulation and changes in optical properties of the irradiated volume of the tissue. To obtain optoacoustic images, the large volume of normal tissue is irradiated by laser pulses with short duration. The pulsed laser radiation penetrates sufficiently deep to heat the volume of the breast tissue with the tumor. Instant heating by short laser pulses produces acoustic (stress) wave with a profile resembling distribution of optoacoustic sources in the tissues. The laser-induced stress wave propagates to the normal tissue surface where it is detected by an acoustic transducer (or transducer array) with sufficient temporal resolution. The transducer signal resembling amplitude and temporal profile of the laser-induced stress wave is recorded via an interface to a computer for signal processing and image reconstruction. The optoacoustic images of the part of the breast with the tumor are displayed in real time. Changes in optical properties due to coagulation result in changes in the optoacoustic images. Dimensions of the coagulation zone are monitored during the continuous wave irradiation. The continuous wave irradiation is blocked, if the tumor is coagulated. This results in accurate coagulation of the tumor with minimal damage to normal breast tissues.

Similar procedures can be used for monitoring of physical properties during coagulation by other types of radiation (microwave, radiofrequency, ultrasonic radiation) as well as treatment by other treatment agents.

EXAMPLE 2

Scheme for Monitoring of Liver Coagulation in Real-time

Figure 3:
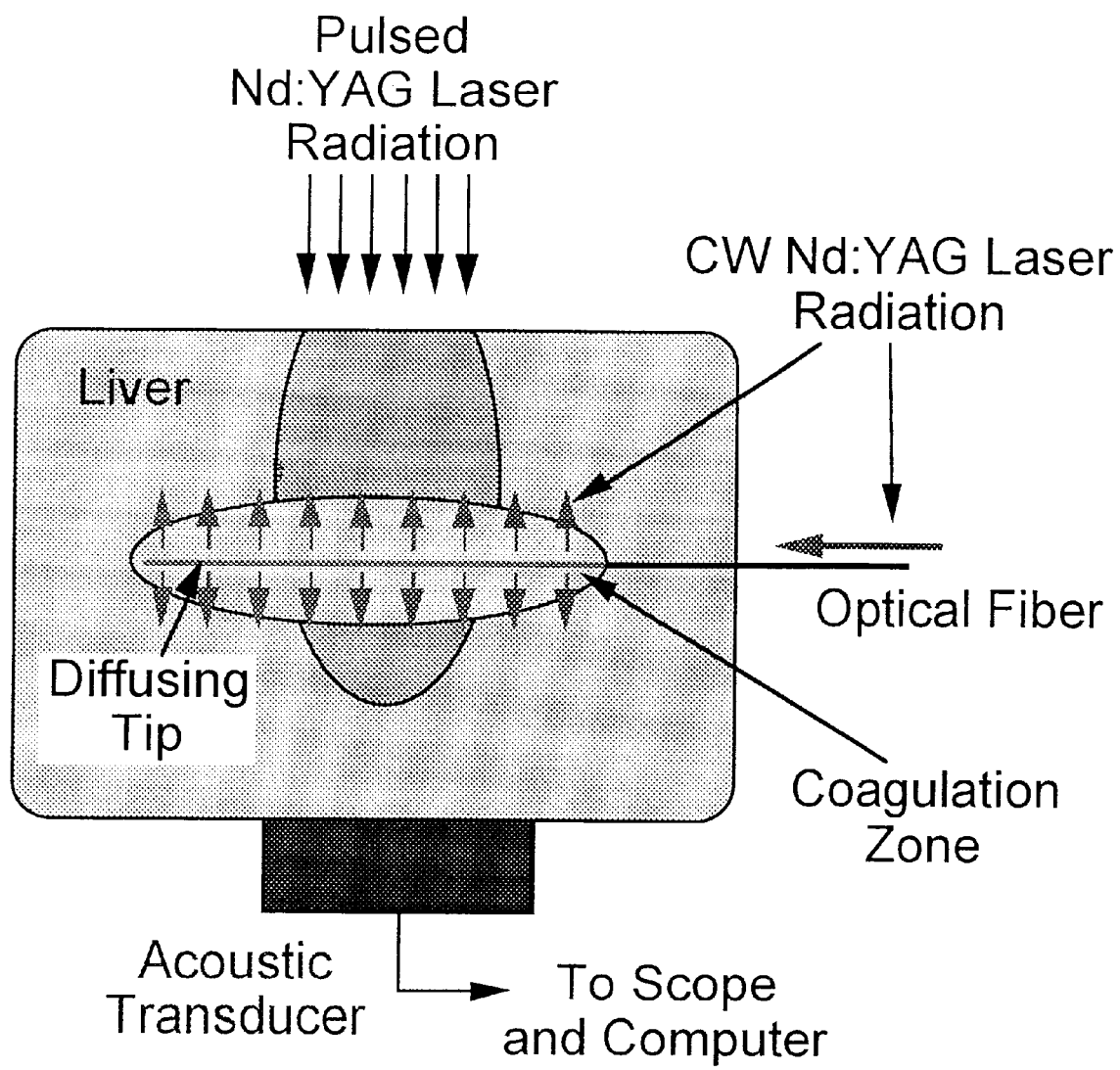
FIG. 3 shows experimental schematics for optoacoustic monitoring of laser interstitial coagulation in real-time.

An experimental scheme for optoacoustic monitoring of liver coagulation in real time is shown in FIG. 3. Freshly excised liver was used in the experiments. Slabs with the dimensions of 50×50 mm were cut from the liver. Thickness of the slabs was varied from 20 to 30 mm. Continuous wave Nd:YAG laser was used to induce coagulation in the liver samples. The continuous wave laser radiation was delivered through a quartz fiber with a specially designed diffusing tip with the length of 25 mm. The diffusing tip scattered radiation in 360° resulting in uniform distribution with cylindrical symmetry. The diffusing tip was introduced into the samples through a needle which was removed from the liver before continuous wave irradiation. Such a scheme allowed coagulation only of a central part of the samples. A Q-switched Nd:YAG laser (pulse duration ~14 ns) was employed for optoacoustic wave generation. The pulsed laser radiation was delivered from above with the use of a prism. Energy of incident laser pulses was 15 mJ. Laser beam diameter was 6 mm providing incident laser fluence of 53 mJ/cm$^2$. The pulsed laser radiation with such parameters induced insignificant temperature rise less than $10^{-3}$ ° C. in the samples. A specially designed sensitive (2.5 V/mbar) acoustic transducers was used to detect optoacoustic pressure waves in a wide spectral range. The samples were placed on the transducer. Data acquisition was performed each 30 s during 1 s. Repetition rate of the pulsed laser radiation was 10 Hz and allowed averaging of 10 pressure wave profiles during this time. The pressure profiles were recorded by a digital scope and stored with a computer.

EXAMPLE 3

Pressure Profiles during Laser Power Induced Coagulation of Liver Tissue

Figure 4:
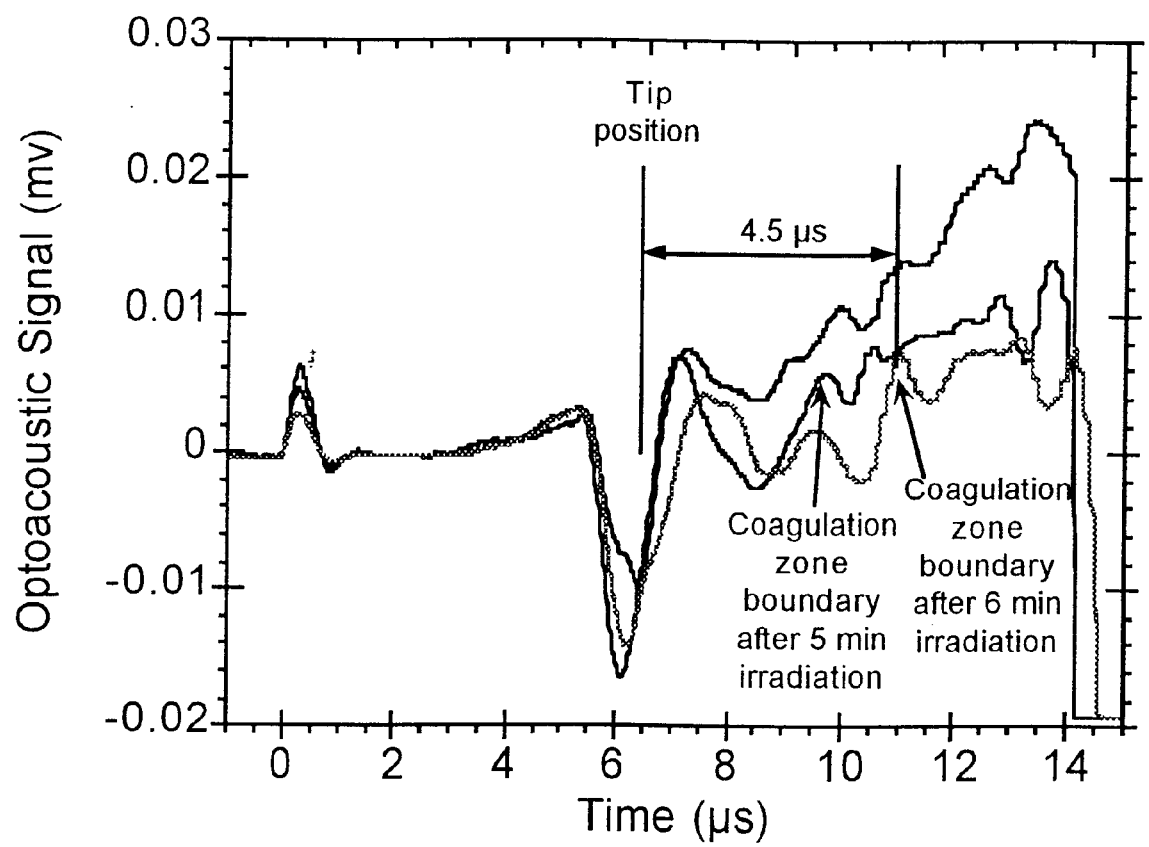
FIG. 4 shows optoacoustic pressure profiles recorded during coagulation of ex vivo canine liver at the laser power of 7 W for 6 minutes.

Pressure profiles recorded during coagulation of canine liver at the laser power of 7 W for 6 minutes are shown in FIG. 4. The first pulse in the profiles was caused by generation of pressure in the acoustic transducer and indicated position of its surface. The pressure profile represents distribution of absorbed pulsed laser energy in the sample. The second pulse was induced in blood accumulated around the diffusing tip after the liver perforation. This pulse indicated the diffusing tip position. The sharp edge at 14 $\mu$s represents the position of the irradiated air-liver interface. It is clearly seen that the profiles change during continuous wave irradiation that indicates changes in optical properties in the sample. The formation of a sharp edge occurs between 8 and 11 $\mu$s during continuous wave irradiation. The delay between the edge and the signal from the diffusing tip is equal to 4.5 $\mu$s at the irradiation time of 6 min. One can calculate the distance between the diffusing tip and the edge by multiplying 4.5 $\mu$s by speed of sound. The speed of sound measured in the normal and coagulated samples is 1.52 and 1.54 mm/$\mu$s, respectively. The calculated value of 6.9 mm is in good agreement with the coagulation zone diameter of 7.0 mm measured after the experiment.

Figure 5:
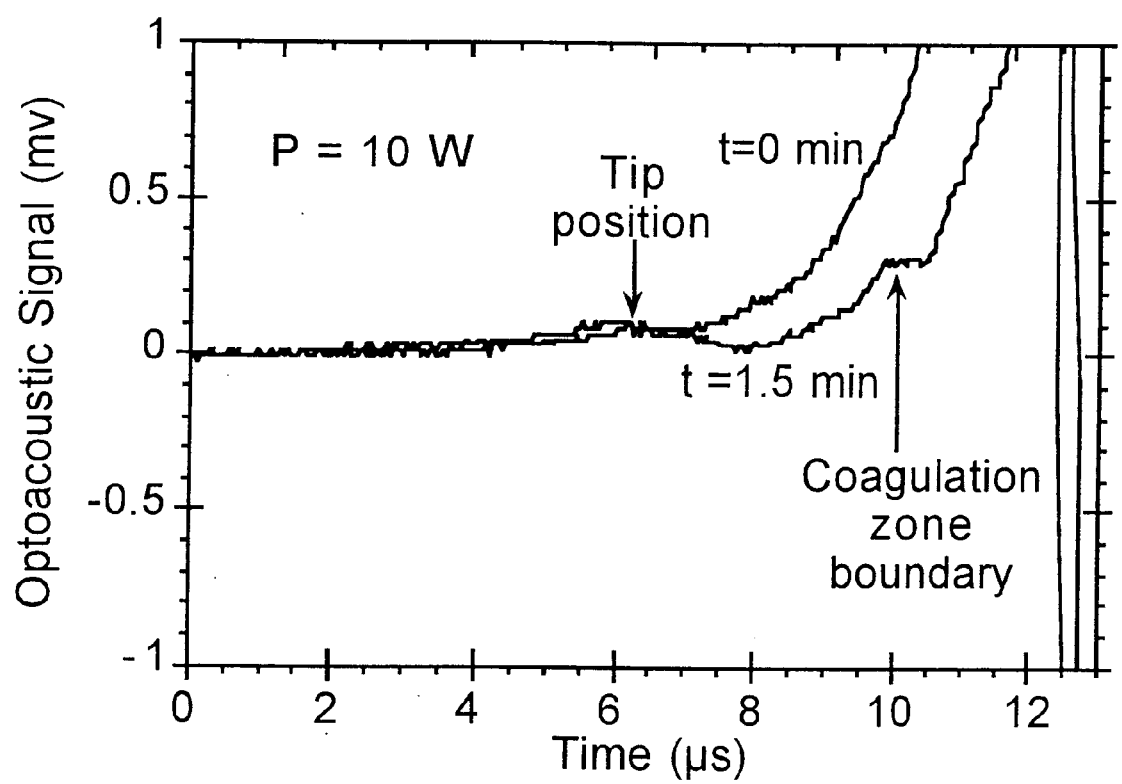
FIG. 5 shows optoacoustic pressure profiles recorded during coagulation of the canine liver at the laser power of 10 W.

Pressure profiles upon continuous wave irradiation with the laser power of 10 W were also recorded and are shown in FIG. 5. The upper profile is measured from a liver sample before the continuous wave irradiation. The lower profile is recorded after 1.5 min. of continuous wave irradiation. The changes in the profile indicates coagulation of the liver tissue near the diffusing tip.

EXAMPLE 4

Monitoring of Microwave Radiation Induced Liver Coagulation

Figure 6:
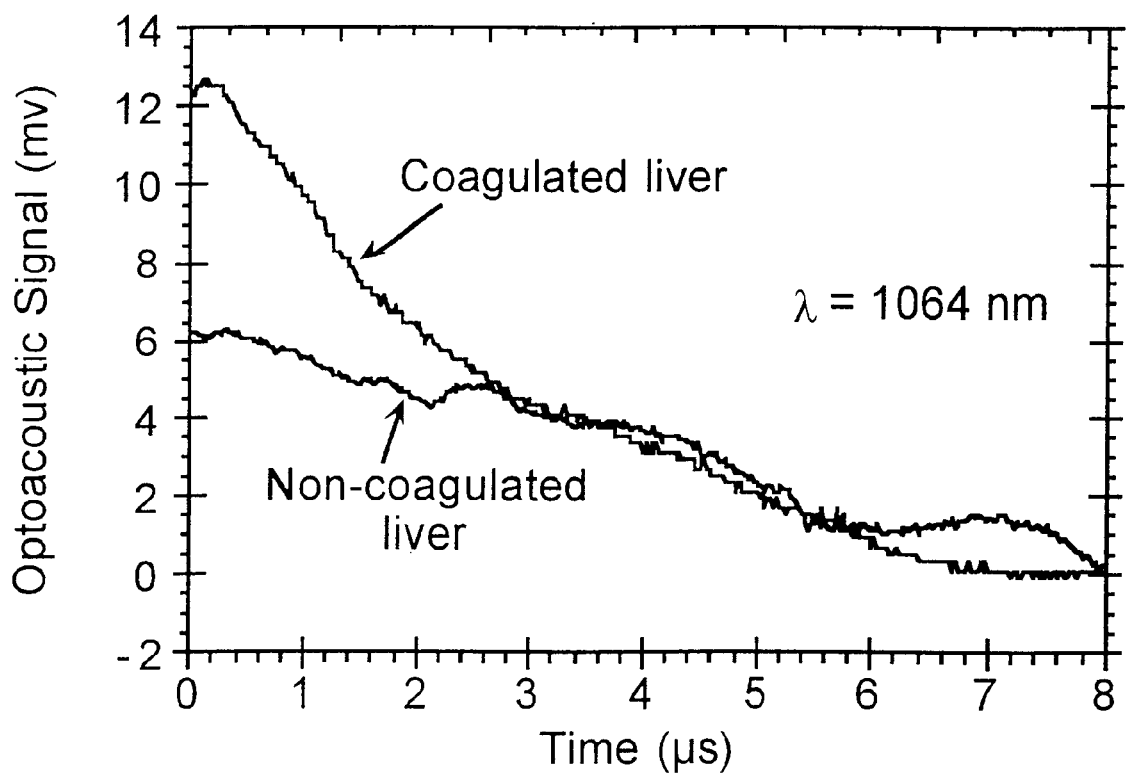
FIG. 6 shows optoacoustic signals recorded from bovine liver samples before and after coagulation by microwave radiation.

Pulsed Nd:YAG laser radiation with the wavelength of 1064 nm was used to generate the thermoelastic pressure waves. No continuous wave laser radiation was applied to the samples. Optoacoustic signals recorded from bovine liver samples before and after coagulation by microwave radiation for 1 min. (see FIG. 6). There is a noticeable difference between these two signals. The pressure amplitude detected from the coagulated tissue is higher than the one recorded from the normal tissue. In addition, the exponential slope for the coagulated tissue is sharper in comparison with the one for the normal one. This indicates that both the absorption and the attenuation coefficient of coagulated tissue is substantially higher than that of the normal one.

Table 1 contains values of optical properties of normal and coagulated liver calculated from experimentally measured pressure profiles. The absorption coefficient of the coagulated tissue is about 2 time higher than that of the normal one. The value of the scattering coefficient increases 2.4 times due to coagulation. The changes in the absorption and scattering coefficients result in 2.2-fold increase of the attenuation coefficient.

TABLE 1

| Optical Property | Normal Liver | Coagulated Liver |
|---|---|---|
| Absorption coefficient (cm$^{-1}$) | 0.42 | 0.82 |
| Scattering coefficient (cm$^{-1}$) | 6.35 | 15.3 |
| Attenuation coefficient (cm$^{-1}$) | 2.92 | 6.3 |

The increase in the attenuation coefficient yields stronger attenuation of Nd:YAG laser radiation in the coagulated zone. This means that this radiation cannot deeply penetrate into the coagulated tissue and that laser fluence in the coagulated zone is substantially lower. Since generated thermoelastic pressure is proportional to the laser fluence, the pressure detected from the coagulated zone is lower than the pressure detected before coagulation from the same zone. This results in the optoacoustic contrast between normal and coagulated tissues.

EXAMPLE 5
Monitoring of Temperature in Aqueous Medium

Figure 7:
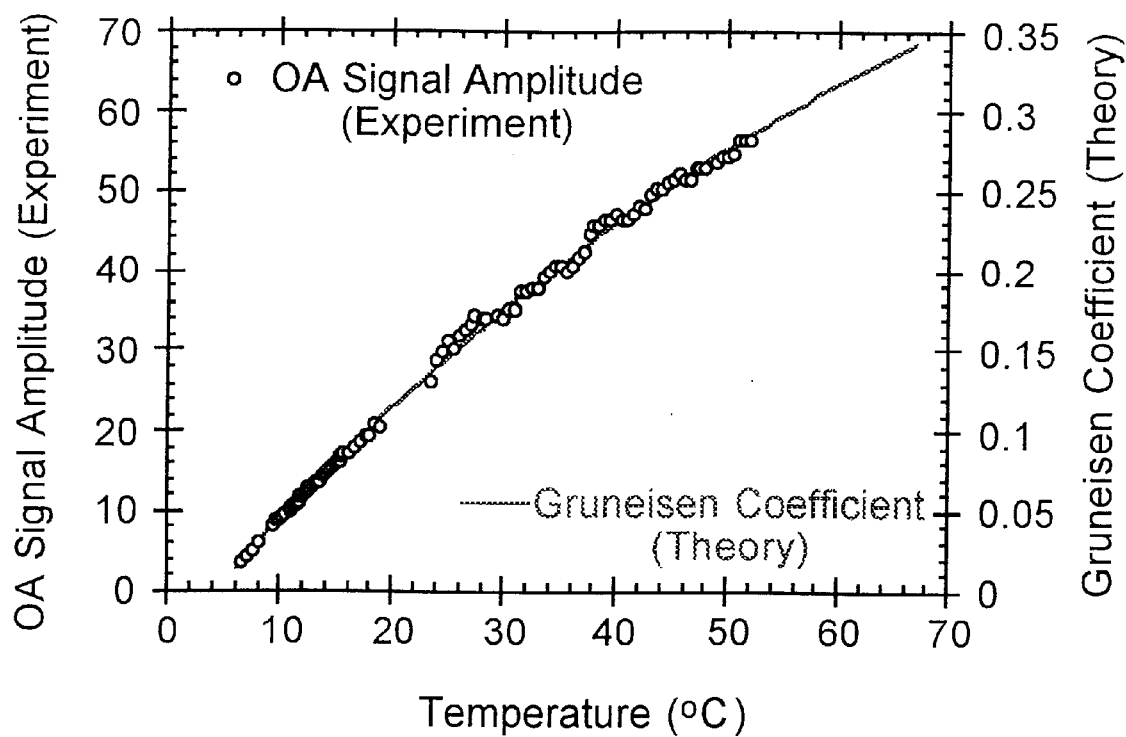
FIG. 7 shows the optoacoustic signal amplitude measured in aqueous solution of potassium chromate as a function of temperature (circles), and the Grüuneisen coefficient theoretically calculated based on published thermomechanical properties of water (solid curve).

The optoacoustic signal amplitude was obtained as a function of temperature measured in aqueous solution of potassium chromate (circles), and the Grüneisen coefficient theoretically calculated based on published thermomechanical properties of water (solid curve) (see FIG. 7). This experiment was performed to demonstrate capability of the laser optoacoustic monitoring technique to measure absolute temperature in aqueous medium. The water solution of potassium chromate was chosen for experiments because optical properties of this solution are not affected by the temperature variations. Therefore, only the Grüneisen coefficient, $\Gamma=\beta C_S^2/C_P$, was influenced by the temperature changes. Thermomechanical properties of the solution, such as $\beta(T)$, the thermoelastic expansion coefficient; $C_S(T)$, the speed of sound; and $C_P(T)$, the heat capacity at constant pressure, are the temperature dependent factors. Laser irradiation wavelength was 355 nm. The temperature rise resulted from laser irradiation was insignificant compared with the base temperature of the solution. A piezoceramic transducer with a 40 MHz bandwidth was used for detection of pressure profiles. The exponential slope of the measured optoacoustic signals was defined by the optical absorption coefficient and was found to be independent on the temperature. Good correlation between theoretical curve and experimental data is evident that temperature measurements in biological tissues may be performed at temperatures below the level of protein coagulation. At temperatures below 54° C. coagulation does not occur and therefore, the changes in the optoacoustic signal amplitude associated with changes in tissue optical properties may be excluded from the consideration.

EXAMPLE 6
Monitoring of Tissue Temperature Change during Hyperthermia

Figure 8:
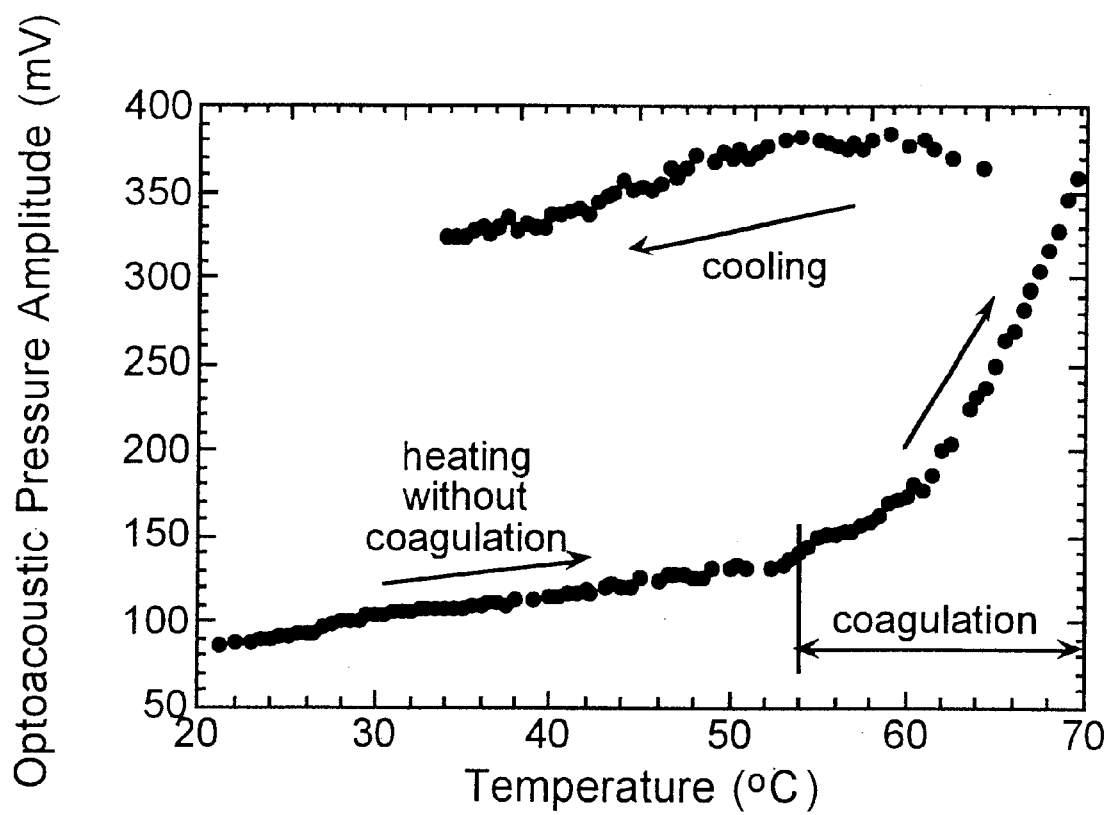
FIG. 8 shows the amplitude of optoacoustic pressure induced in freshly excised canine liver as a function of temperature during hyperthermia and coagulation.

Amplitude of optoacoustic pressure induced in freshly excised canine liver during hyperthermia and coagulation was measured and shown to be temperature dependent (see FIG. 8). The measurements were performed in real time during heating and cooling of the tissue. The tissue was heated by hot air for 30 min. To avoid desiccation, the tissue was covered by a plastic film. It is clearly seen that the amplitude is increasing linearly with the increase of the temperature from 22 to about 54° C. Changes in optical properties induced by coagulation result in the sharp increase of the pressure amplitude at the temperature above 52° C. Subsequent cooling leads to gradual decrease of pressure amplitude.

Figure 9:
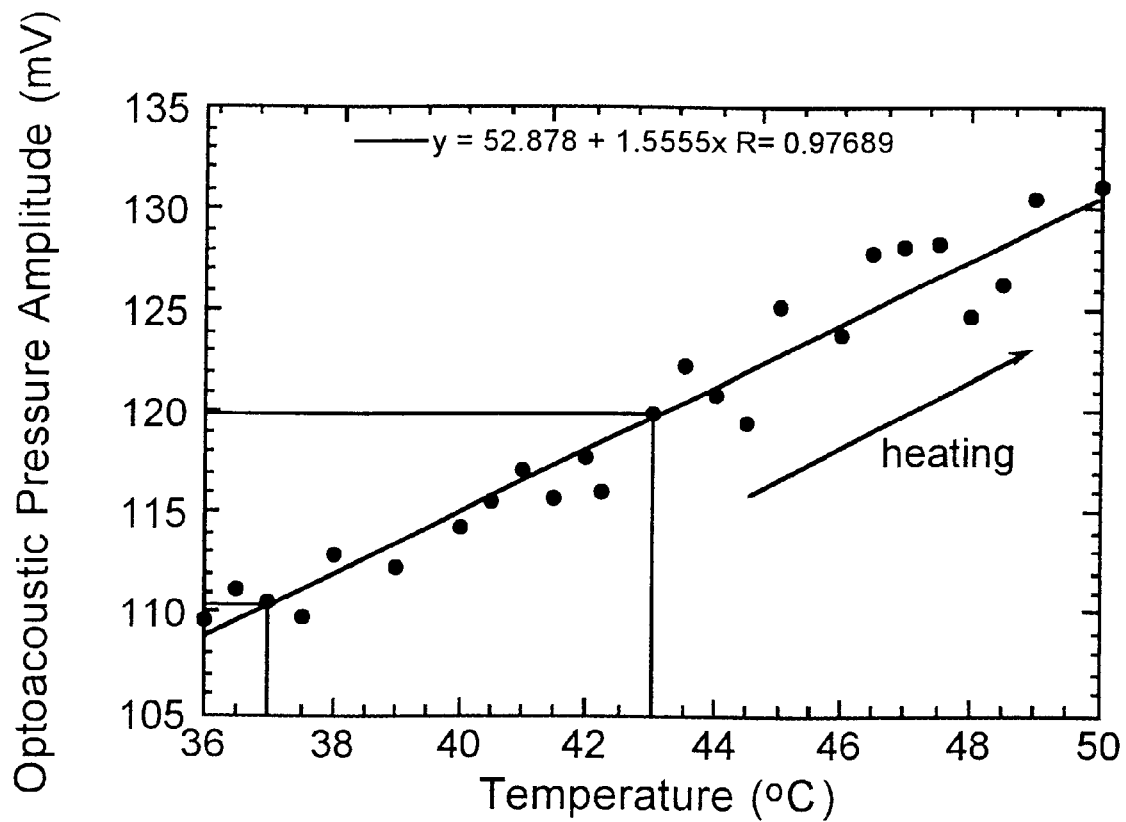
FIG. 9 shows the amplitude of optoacoustic pressure induced in the canine liver as a function of temperature during hyperthermia between 36 and 50° C. without coagulation.

Amplitude of optoacoustic pressure induced in the canine liver during hyperthermia between 36 and 54° C. without coagulation was also measured (see FIG. 9). The data shows that the amplitude of optoacoustic pressure was also temperature dependent. The relative increase in pressure amplitude amounts approximately 1.5% per 1° C. that results in about 9% pressure amplitude increase if the liver is heated from 36 to 54° C. This temperature rise is normally applied for hyperthermia. These results indicate that by detecting the pressure wave amplitude with sufficient accuracy, one can monitor temperature rise in tissues. The accuracy of temperature measurements was about 3% in this experiment and was limited by instability of laser energy (10%). Current laser systems with stabilized pulse energy available on the market have 1%-stability, therefore the accuracy of temperature measurement of about 0.3% can be achieved. The increase of pressure amplitude with the increase of temperature is noticeable and substantially greater than changes in acoustic properties (speed of sound and density) and chemical content of the tissue. This results in exceptional contrast of optoacoustic images compared with the contrast of ultrasound and MRI images.

Figure 10:
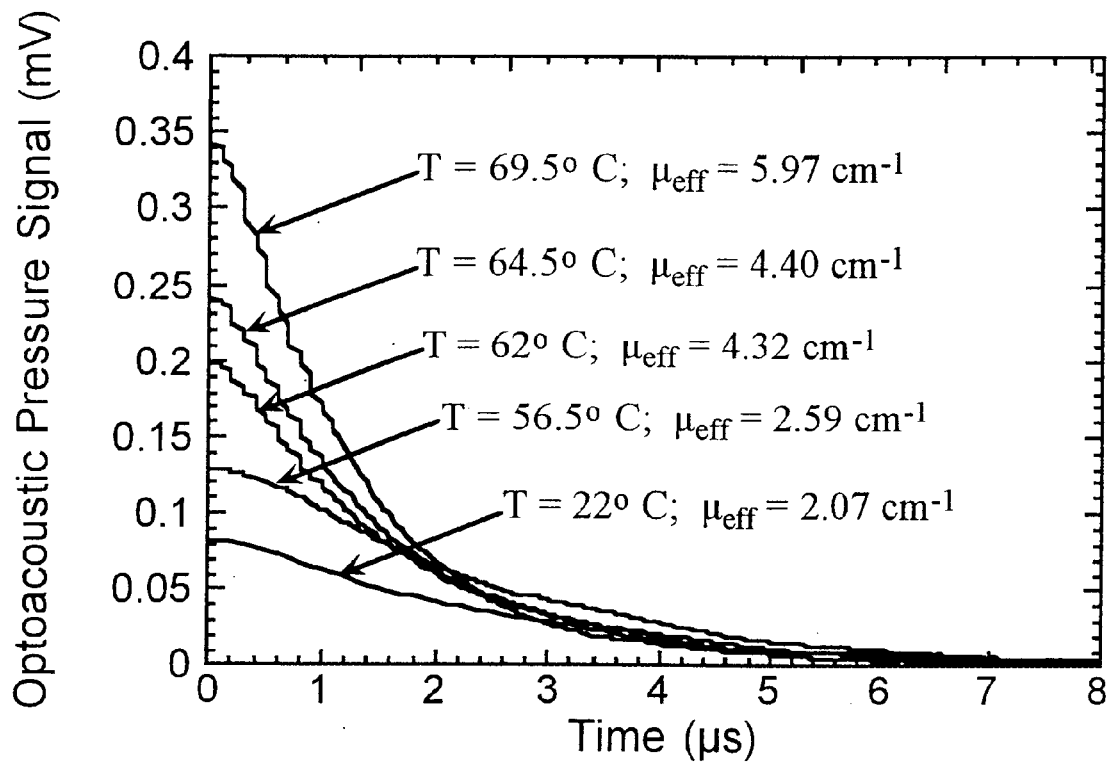
FIG. 10 shows optoacoustic pressure profiles recorded in real time from the normal and coagulated canine liver during coagulation.

EXAMPLE 7
Comparison of Tissue Properties between Normal and Coagulated Liver Tissue Optoacoustic pressure profiles from the normal and coagulated canine liver were recorded (see FIG. 10). Pressure profiles recorded from coagulated liver differ dramatically from those recorded from the normal liver. Due to an increase i n attenuation coefficient, the profiles recorded from the coagulated tissue were substantially sharper than the profiles recorded from the normal one.

Figure 11:
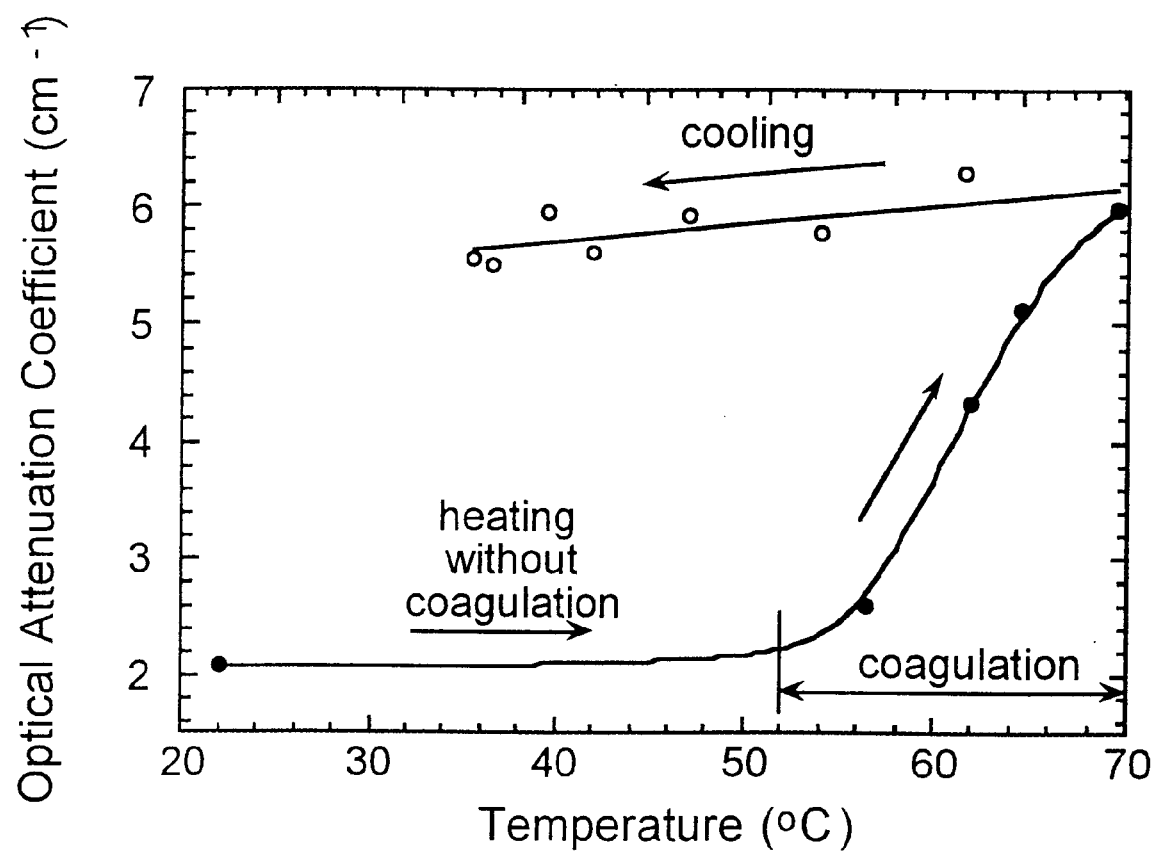
FIG. 11 shows optical attenuation coefficients of the coagulated and normal canine liver as a function of temperature.

The optical attenuation coefficient of the coagulated and normal canine liver was shown to be temperature dependent (see FIG. 11). The attenuation coefficient of coagulated tissue at the temperature of about 70° C. was 4 times greater than the one of normal liver at this heating conditions. Data analysis indicates that these changes are due to approximately 4-fold increase of absorption and scattering coefficient of the liver induced by coagulation. These results explain formation of the sharp edge in the detected pressure profiles. The edge is caused by strong attenuation of laser radiation in the coagulated zone. The movement of the edge from the diffusing tip indicates an increase of coagulation zone dimensions during continuous wave laser irradiation.

EXAMPLE 8
Monitoring of Myocardium Coagulation during Heating

Figure 12:
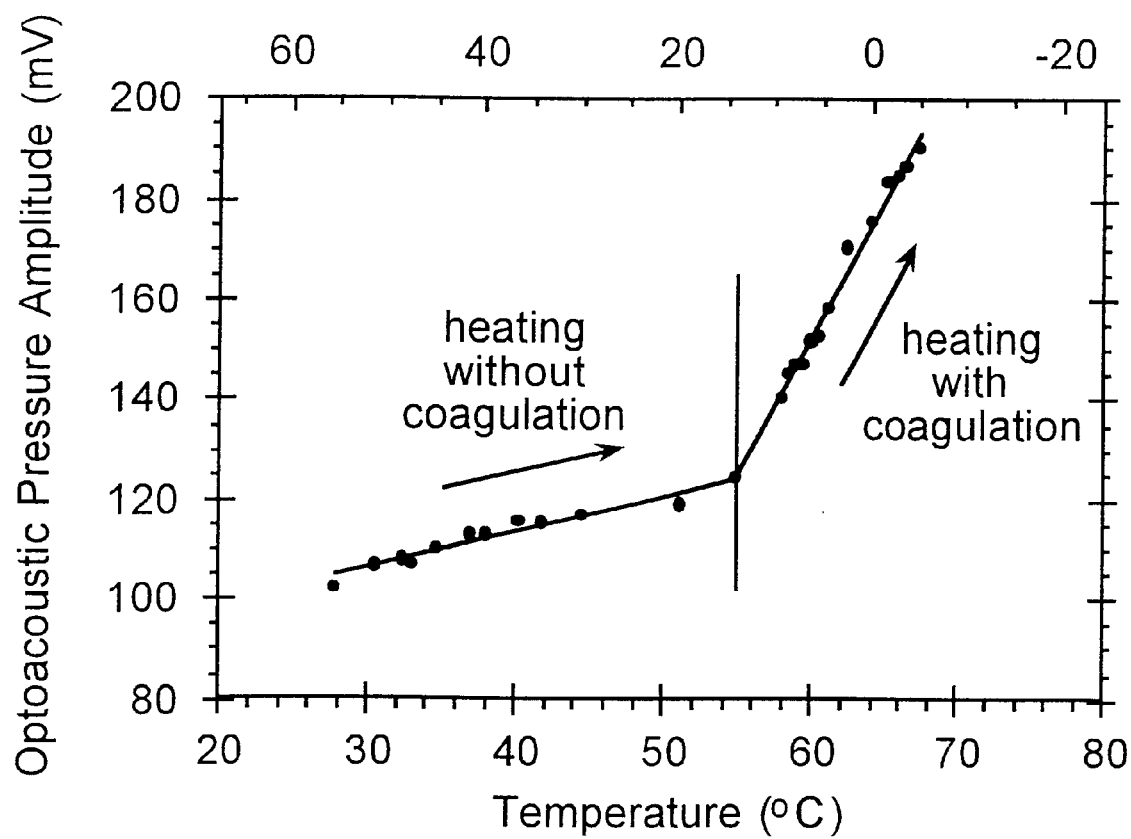
FIG. 12 shows the amplitude of optoacoustic pressure as a function of temperature during heating of freshly excised canine myocardium.

The amplitude of optoacoustic pressure was measured in real time from freshly excised canine myocardium during heating by hot air for 30 min. (see FIG. 12). The data shows that the amplitude is temperature dependent. To avoid desiccation, the tissue was covered by a thin plastic film. The pressure amplitude was shown to increase linearly with the increase of the temperature from 26° C. to about 55° C. Changes in optical properties induced by coagulation resulted in a sharp increase of the pressure amplitude at the temperature above 55° C. Optical attenuation coefficients of normal and coagulated myocardium calculated from pressure profiles equal 3.32 $cm^{-1}$ and 4.29 $cm^{-1}$, respectively. These data demonstrate that real-time measurements of pressure amplitude and attenuation coefficient can be used for monitoring myocardium coagulation.

Figure 13:
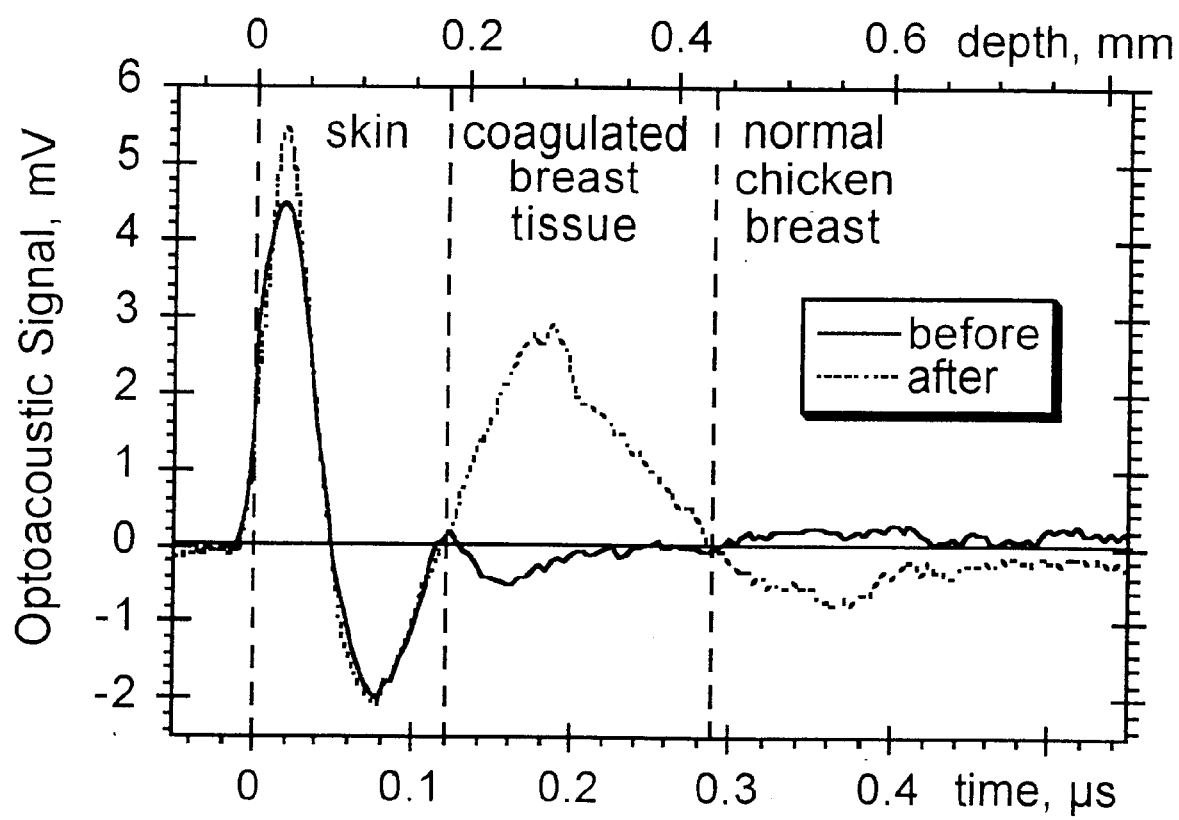
FIG. 13 shows a laser-induced pressure profile measured with an optoacoustic transducer from a chicken breast muscle slab covered with skin (solid curve) and the same tissues where the top layer of the muscle slab was coagulated (dashed curve).

EXAMPLE 9
Laser-Induced Pressure Profile Measured with an Optoacoustic Transducer A laser-induced pressure profile was measured with an optoacoustic transducer from a chicken breast muscle slab covered with skin (solid curve) and the same tissues where the top layer of the muscle slab was coagulated (dashed curve) (see FIG. 13). Laser irradiation wavelength was 532 nm. Lithium niobate front-surface optoacoustic transducer with a 100 MHz bandwidth was used for detection of pressure profiles.

The optoacoustic profile was first measured in a fresh chicken breast muscle covered with skin. The measured optoacoustic signal shows two layers: skin and muscle tissues. The optical absorption of chicken breast is slightly higher than that of the chicken skin. This allows optoacoustic imaging of the two layers. Acoustic diffraction that occurs in the prism of the optoacoustic transducer converts the intrinsic signal into its derivative. That is why originally positive pressure signals were measured as bipolar signals.

The top layer of the breast muscle was then placed for 1 minute in water heated to 100° C., and therefore, coagulated. The protein coagulation process dramatically increased tissue optical scattering. The increased tissue scattering resulted in enhanced amplitude of the measured optoacoustic signal. Three layers of optoacoustically different tissue can be detected after coagulation. The optoacoustic signal amplitude sharply increased at the boundary between skin and coagulated chicken breast. The optoacoustic signal amplitude decreased at the boundary between coagulated and normal chicken breast. The thickness of the top layer of skin and the coagulated layer can be measured from the presented profiles with a 30-$\mu$m accuracy. The result demonstrates capability of the optoacoustic imaging system to monitor tissue coagulation zone with the accuracy of tens of microns.

Discussion

The obtained results demonstrate that the optoacoustic technique can be successfully applied for monitoring of interstitial tissue temperature and coagulation in real time. The optoacoustic technique has such advantages compared with conventional imaging techniques as: (1) high contrast, (2) high sensitivity, (3) moderate cost, (4) minimal invasiveness, (5) capability of monitoring in real time. Currently investigated optical imaging techniques based on contrast in optical properties can also provide high contrast. However, they are not capable of monitoring tissue optical properties at the depth of the order of centimeters.

The following references were referred to herein.
1. Kruger, R. A. U.S. Pat. No. 5,713,356.
2. Tauc, J., et. al. U.S. Pat. No. 4,710,030.
3. Bowen, T. U.S. Pat. No. 4,385,634.
4. Oraevsky, A. A., et al., In: "Advances in Optical Imaging and Photon Migration", vol. 21, ed. by Robert R. Alfano, Academic Press, 1994, pp.161–165.
5. Thomsen, S., et al., SPIE Proc. 1994, v. 2134, pp. 106–113.
6. Oraevsky A. A., et al., SPIE Proc. 1994, v. 2134, pp. 122–128.
7. Motamedi M., et al., Laser Surg. Med., 1995, v. 17, pp. 49–58.
8. Oraevsky A. A., et al., SPIE Proc. 1995, v. 2389, pp. 198–208.
9. Agah, et al., IEEE Trans. Biomed. Eng. 1996, 43 (8), pp. 839–846.
10. Oraevsky A. A., et al., SPIE Proc. 1996, v. 2676, pp. 22–31.
11. Esenaliev R. O., et al., SPIE Proc. 1996, v. 2676, pp. 84–90.
12. Oraevsky A. A., et al., In: "Trends in Optics and Photonics", 1996, vol. II, ed. by R R Alfano and J G Fujimoto, OSA Publishing House, pp. 316–321.
13. Kim B., et al., IEEE J. Quant. Electr., 1996, v. 2 (4), pp. 922–933.
14. Karabutov A. A., et al., Appl. Phys. B, 1996, v.63, pp.545–563.
15. Oraevsky A. et al., Applied Optics, 1997, v. 36 (1), pp. 402–415.
16. Oraevsky A. A., et al., SPIE Proc. 1997, v. 2979, pp. 59–70.
17. Esenaliev R. O., et al., SPIE Proc. 1997, v. 2979, pp. 71–82.
18. Esenaliev R. O., et al., SPIE Proc. 1998, v. 3254, pp. 294–301.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of monitoring tissue properties in real time during treatment using laser optoacoustic imaging comprising the steps of:

administering a treatment agent to tissue of interest;

irradiating a volume of said tissue with at least one laser pulse so as to penetrate said tissue and selectively heat a small volume or layer of said tissue with a higher optical absorption causing the tissue to produce a pressure profile confined in said volume or layer of said tissue, wherein said pressure profile reflects a value of pressure as a function of depth in said tissue, and wherein said pressure profile is characteristic of said tissue;

wherein said at least one irradiating laser pulse is different from said treatment agent and wherein said treatment agent is electromagnetic radiation which is in a radiofrequency or in a microwave spectral range or which is a X-ray or a gamma radiation;

detecting said pressure profile with at least one acoustic transducer;

recording an amplitude and temporal profile of said pressure profile by an electronic system; and analyzing said pressure profile with a computer.

2. The method of claim 1, wherein said tissue properties are selected from the group consisting of physical dimension, optical absorption, optical scattering, optical attenuation coefficient, temperature, thermal expansion coefficient, speed of sound, and heat capacity.

3. The method according to claim 1, wherein said electromagnetic radiation is delivered through the same fiber-optic delivery system as are optical pulses for imaging.

4. The method of claim 1, wherein said transducer determines a geometry of the monitored tissue volume by positioning a multiple of acoustic transducers at fixed locations along the surface of said monitored tissue.

5. The method of claim 1, wherein multiple separate optical fibers or laser beams irradiate a large volume of tissue to reduce time of scanning and incident laser fluence.

6. The method of claim 1, wherein said pressure profile detection is in forward signal propagation mode as said irradiation and said acoustic detection are performed at different sites in said tissue.

7. The method of claim 1, wherein said pressure profile detection occurs at a tissue depth of up to about 12 cm measured from an irradiated surface.

8. The method of claim 1, wherein said pressure profile detection is in backward signal propagation mode as said irradiation and said acoustic detection are performed at a same site in said tissue.

9. The method of claim 1, wherein said irradiating is in a spectral range of from about 600 nm to about 1400 nm.

10. The method of claim 1, wherein said tissue is an internal organ with tumor(s) or other lesion(s), and wherein irradiation is delivered via an endoscope to a first tissue and said acoustic transducer is positioned on a second tissue surface opposite said first tissue surface.

11. The method of claim 1, wherein said tissue is an internal organ with tumor(s) or other lesion(s), and wherein irradiation is delivered onto a first tissue surface and said transducer is incorporated with an endoscope and positioned at a second tissue surface opposite said first tissue surface.

12. The method of claim 1, wherein said tissue is an internal organ with tumor(s) or other lesion(s), and wherein an optical fiber and said transducer are incorporated in an endoscope and positioned inside the organ such that irradiation and detection is performed from the same site at the internal surface of said organ.

13. The method of claim 1, wherein said pressure profile is recorded simultaneously from a number of sites along a surface of said tissue in order to reconstruct a two-dimensional or three-dimensional tomographic image.

14. The method of claim 1, wherein said detecting step is performed by scanning of a single transducer along said tissue.

15. The method of claim 1, wherein said detecting step is performed by scanning of an array of transducers along said tissue.

16. The method of claim 1, wherein said tissue is selected from the group consisting of breast tumor tissue, prostate tissue, brain tissue, skin tissue, ocular tissue, and blood vessel tissue.

17. The method of claim 1, further comprising the step of:
contacting said tissue with an exogenous molecular probe whose properties change in response to said treatment.

18. The method of claim 1, wherein said treatment agent is electromagnetic radiation which is in a radiofrequency or in a microwave spectral range.

19. The method of claim 1, wherein said treatment agent is electromagnetic radiation which is a X-ray or a gamma radiation.

20. A method of monitoring tissue properties in real time during treatment using laser optoacoustic imaging comprising the steps of:
administering a treatment agent to tissue of interest;
irradiating a volume of said tissue with at least one laser pulse so as to penetrate said tissue and selectively heat a small volume or layer of said tissue with a higher optical absorption causing the tissue to produce a pressure profile confined in said volume or layer of said tissue, wherein said pressure profile reflects a value of pressure as a function of depth in said tissue, and wherein said pressure profile is characteristic of said tissue;
wherein said at least one irradiating laser pulse is different from said treatment agent;
detecting said pressure profile with at least one acoustic transducer;
recording an amplitude and temporal profile of said pressure profile by an electronic system; and
analyzing said pressure profile with a computer;
wherein said method further comprises the step of:
contacting said tissue with an exogenous molecular probe whose properties change in response to said treatment.

21. The method of claim 20, wherein said tissue properties are selected from the group consisting of physical dimension, optical absorption, optical scattering, optical attenuation coefficient, temperature, thermal expansion coefficient, speed of sound, and heat capacity.

22. The method of claim 20, wherein said treatment agent is selected from the group consisting of an electromagnetic radiation, an ultrasonic radiation, an electrical current, heating, cooling, a drug, and a surgical tool.

23. The method of claim 22, wherein said treatment agent is optical radiation.

24. The method of claim 23, wherein said optical radiation is delivered through the same fiber-optic delivery system as are optical pulses for imaging.

25. The method of claim 22, wherein said treatment agent is electromagnetic radiation which is in a radiofrequency or in a microwave spectral range or which is a X-ray or a gamma radiation.

26. The method of claim 20, wherein said transducer determines a geometry of the monitored tissue volume by positioning a multiple of acoustic transducers at fixed locations along the surface of said monitored tissue.

27. The method of claim 20, wherein multiple separate optical fibers or laser beams irradiate a large volume of tissue to reduce time of scanning and incident laser fluence.

28. The method of claim 20, wherein said pressure profile detection is in forward signal propagation mode as said irradiation and said acoustic detection are performed at different sites in said tissue.

29. The method of claim 20, wherein said pressure profile detection occurs at a tissue depth of up to about 12 cm measured from an irradiated surface.

30. The method of claim 20, wherein said pressure profile detection is in backward signal propagation mode as said irradiation and said acoustic detection are performed at a same site in said tissue.

31. The method of claim 20, wherein said irradiating is in a spectral range of from about 600 nm to about 1400 nm.

32. The method of claim 20, wherein said tissue is an internal organ with tumor(s) or other lesion(s), and wherein irradiation is delivered via an endoscope to a first tissue and said acoustic transducer is positioned on a second tissue surface opposite said first tissue surface.

33. The method of claim 20, wherein said tissue is an internal organ with tumor(s) or other lesion(s), and wherein irradiation is delivered onto a first tissue surface and said transducer is incorporated with an endoscope and positioned at a second tissue surface opposite said first tissue surface.

34. The method of claim 20, wherein said tissue is an internal organ with tumor(s) or other lesion(s), and wherein an optical fiber and said transducer are incorporated in an endoscope and positioned inside the organ such that irradiation and detection is performed from the same site at the internal surface of said organ.

35. The method of claim 20, wherein said pressure profile is recorded simultaneously from a number of sites along a surface of said tissue in order to reconstruct a two-dimensional or three-dimensional tomographic image.

36. The method of claim 20, wherein said detecting step is performed by scanning of a single transducer along said tissue.

37. The method of claim 20, wherein said detecting step is performed by scanning of an array of transducers along said tissue.

38. The method of claim 20, wherein said tissue is selected from the group consisting of breast tumor tissue, prostate tissue, brain tissue, skin tissue, ocular tissue, and blood vessel tissue.

* * * * *